United States Patent
Franz et al.

(10) Patent No.: US 11,617,624 B2
(45) Date of Patent: Apr. 4, 2023

(54) SYSTEM FOR NAVIGATED PUNCTION, BIOPSY OR ABLATION COMPRISING A NEEDLE-LIKE INSTRUMENT AND A REMOVABLE SENSOR CARRIER

(71) Applicant: Deutsches Krebsforschungszentrum Stiftung des öffentlichen Rechts, Heidelberg (DE)

(72) Inventors: Alfred Franz, Heidelberg (DE); Lena Maier-Hein, Heidelberg (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 205 days.

(21) Appl. No.: 16/083,029

(22) PCT Filed: Mar. 6, 2017

(86) PCT No.: PCT/EP2017/055137
§ 371 (c)(1),
(2) Date: Sep. 7, 2018

(87) PCT Pub. No.: WO2017/153312
PCT Pub. Date: Sep. 14, 2017

(65) Prior Publication Data
US 2019/0090956 A1    Mar. 28, 2019

(30) Foreign Application Priority Data
Mar. 7, 2016  (EP) ..................... 16158995

(51) Int. Cl.
*A61B 34/20*    (2016.01)
*A61B 90/00*    (2016.01)
*A61B 17/00*    (2006.01)

(52) U.S. Cl.
CPC .............. *A61B 34/20* (2016.02); *A61B 90/39* (2016.02); *A61B 2017/00486* (2013.01);
(Continued)

(58) Field of Classification Search
CPC .................... A61B 34/20; A61B 90/39; A61B 2017/00486; A61B 2034/2051; A61B 2090/3954; A61B 2090/397
See application file for complete search history.

(56) References Cited

U.S. PATENT DOCUMENTS 6,216,029 B1    4/2001    Paltieli
2006/0063973 A1*    3/2006    Makower ............... A61B 1/267
600/114

(Continued)

FOREIGN PATENT DOCUMENTS

DE    202015106804    1/2016

OTHER PUBLICATIONS

European Patent Office, International Search Report and Written Opinion, PCT/EP2017/055137; dated Apr. 13, 2017. 14 pages.

*Primary Examiner* — Joseph M Santos Rodriguez
*Assistant Examiner* — Kaitlyn E Sebastian
(74) *Attorney, Agent, or Firm* — Sunstein LLP

(57) ABSTRACT

Disclosed herein is a system for navigated punction, biopsy or ablation comprising a mobile electromagnetic field generator for generating an electromagnetic navigation field which is connected to an apparatus for medical imaging, a needle-like instrument (16), comprising a sterile distal portion (22) and an optionally non-sterile proximal portion (20), a removable protection device (30) for encapsulating the sterile distal portion (22), a sensor (38) suitable for carrying out measurements allowing for determining the position of the sensor (38) within the navigation field, and a sensor carrier (26). The sensor carrier (26) comprises an elongate (Continued)

carrier body (36) having proximal and distal ends. The sensor (38) is attached to or enclosed by said carrier body (36) close to its distal end. A connection mechanism (32) is provided allowing to releasably connect said sensor carrier (36) with the non-sterile proximal portion (22) such that said elongate carrier body (36) extends from said connection position in distal direction.

11 Claims, 1 Drawing Sheet

(52) U.S. Cl.
CPC .. *A61B 2034/2051* (2016.02); *A61B 2090/397* (2016.02); *A61B 2090/3954* (2016.02)

(56) References Cited

U.S. PATENT DOCUMENTS

| | | | |
|---|---|---|---|
| 2010/0234724 A1* | 9/2010 | Jacobsen | A61B 90/37 600/424 |
| 2011/0137156 A1 | 6/2011 | Razzaque et al. | |
| 2011/0238043 A1 | 9/2011 | Kleven | |
| 2011/0295109 A1 | 12/2011 | Lavallee et al. | |
| 2012/0016316 A1* | 1/2012 | Zhuang | A61B 5/150748 604/246 |
| 2014/0024945 A1* | 1/2014 | Mung | A61B 8/0841 600/461 |
| 2017/0095234 A1* | 4/2017 | Prisco | A61B 34/35 |

\* cited by examiner

SYSTEM FOR NAVIGATED PUNCTION, BIOPSY OR ABLATION COMPRISING A NEEDLE-LIKE INSTRUMENT AND A REMOVABLE SENSOR CARRIER

CROSS-REFERENCE TO RELATED APPLICATIONS

This application is the national phase entry of international patent application no. PCT/EP2017/055137, filed Mar. 6, 2017 and claims the benefit of European patent application No. 16 158 995.7, filed Mar. 7, 2016, the disclosures of which are incorporated herein by reference in their entirety.

FIELD OF THE INVENTION

The present invention is in the field of medical technology. More particularly, the present invention relates to a system for navigated punction, biopsy or ablation comprising a needle-like instrument and a sensor carrier attachable thereto.

BACKGROUND OF THE INVENTION

For computer-assisted interventions, ultrasound offers several benefits over other imaging modalities. It acquires images in real time and at low costs, is widely available and does not expose the patient or the physician to radiation. However, most computer assisted interventions require exact localization, typically referred to as "tracking" in the art, of instruments and patient. Whenever image-based tracking is not feasible, external tracking systems are a common alternative. Electromagnetic tracking is a technique which enables the localization of small sensors in an electromagnetic field without the need of a line of sight. However, an additional device, the electromagnetic field generator needs to be placed near to the patient. This complicates the integration of such systems into the clinical workflow and hinders wide clinical application.

In view of these difficulties, a new tracking scheme referred to as "EchoTrack" has been recently proposed and is further described in the following articles co-authored by the present inventors: K. März et al.; "Mobile EM Field Generator for Ultrasound Guided Navigated Needle Insertions"; IPCAI; L. Maier-Hein et al.; "Standardized assessment of new electro-magnetic field generators in an interventional radiology setting"; 3424 *Med. Phys.* 39(6), June 2012; A. Winterstein et al.; "Navigated Marker Placement for Motion Compensation in Radiotherapy"; SPIE2015; K März et al.; "Interventional real-time ultrasound imaging with an integrated electromagnetic field generator"; *Int J CARS*, 2013.

EchoTrack integrates a new mobile electromagnetic field generator and an ultrasound probe in one single device and thus allows for simultaneous real-time localization of patient and instrument. It employs the following key advantages in comparison to previous systems: (1) No additional external hardware is required as the field generator is directly integrated into the handheld EchoTrack probe, which simplifies workflow integration. (2) Moving the field generator together with the probe implies high precision and accuracy, since the area of interest automatically and continuously is situated near the center of the tracking volume. Initial validation studies performed with a research prototype of EchoTrack indicate that the concept allows for accurate tracking in clinical environments and that distortions caused by the attached ultrasound probes can be neglected when suitable probes are used. For validation in a clinical context, a prototype system for navigated needle insertion based on EchoTrack was successfully assessed in phantom and animal studies, yielding a targeting error of 3-4 mm only.

The EchoTrack scheme is particularly useful for navigated punction, biopsy or ablation using needle-like instruments. In the present disclosure, the term "needle-like instrument" shall have a broad meaning and cover all types of elongate instruments which can be used for punction, biopsy or ablation. In order to track the needle-like instrument, a sensor suitable for carrying out a measurements allowing for determining the position of the sensor within the electromagnetic field needs to be associated with the instrument. Such sensor could for example be integrated in the tip of a needle. However, this requires specially manufactured needles for this purpose, which increases the costs. This is of particular concern since such needles are usually provided as disposable products.

These difficulties can be avoided if the sensor is not integrated with the needle-like instrument, but is somehow removably connected with the instrument, so that it can be reused even if the instrument as such is disposed after use. In external tracking applications, it has been proposed to attach the sensor to a sterile portion of the needle. However, this means that the sensor itself also needs to be made sterile, or be included in a sterile encapsulation of some sort, which is not only cumbersome, but also bears a certain risk that sterility cannot be ensured.

For external tracking systems, there have also been made attempts to releasably connect a sensor to a handle portion of a needle, which handle portion need not necessarily be sterile under operation, such that the same relaxed requirement applies for the sensor. However, with handle attached sensors, it proves difficult to ensure a desired tracking precision. This is particulary true in EchoTrack applications, where the electromagnetic field is confined to a limited spatial area.

SUMMARY OF THE INVENTION

The problem underlying the invention is to provide a system for navigated punction, biopsy or ablation which allows for cost efficient components, easy use and yet good navigation precision, as well as to provide components for use in such a system.

This problem is solved by a system for navigated punction, biopsy or ablation according to claim 1, as well as a sensor carrier according to claim 12 and a set comprising such sensor carrier and a needle-like instrument according to claim 14. Preferable embodiments are defined in the dependent claims.

The system of the invention comprises a mobile electromagnetic field generator for generating an electromagnetic navigation field, which field generator is connected to an apparatus for medical imaging, in particular to an ultrasound probe.

The system further comprises a needle-like instrument, comprising a sterile distal portion and an optionally non-sterile proximal portion, and a removable protection device for encapsulating the sterile portion. Herein, the "sterile distal portion" comprises the portion of the needle-like instrument that is actually inserted to the patient's tissue upon use and therefore necessarily must be sterile prior to use. In contrast to this, the "optionally non-sterile proximal portion" is a proximal portion which upon use is not intended to come in contact with the patient's tissue and hence need not necessarily be sterile. For example, the optionally non-sterile portion could include a handle where the instrument is held by the surgeon upon use. Herein, the term "optionally" non-sterile shall indicate that—unlike the sterile distal portion—this portion need not necessarily be sterile, although it may of course be made sterile if this is desired.

The system further comprises a sensor suitable for carrying out measurements allowing for determining the position of the sensor within the navigation field.

Finally, the system comprises a sensor carrier, wherein:
said sensor carrier comprises an elongate carrier body having proximal and distal ends,
said sensor is attached to or enclosed by said carrier body close to its distal end, and
a connection mechanism is provided allowing to releasably connect said sensor carrier with the non-sterile proximal portion at a predetermined connection position and with a predetermined orientation of said sensor carrier body with respect to said needle-like instrument, such that when said sensor carrier is connected with said instrument via said connection mechanism,
said elongate carrier body extends from said connection position in distal direction, and
said sensor is automatically located at a predetermined and known position relative to the distal end of said sterile distal portion.

Herein, the "distal end" of said sterile distal portion is typically a tip of said needle-like instrument.

According to the invention, prior to using the needle-like instrument in the surgical intervention, the sensor carrier is connected with the non-sterile proximal portion of said needle-like instrument, by means of said connection mechanism, at a predetermined connection position which is located on the non-sterile proximal portion. In other words, the sensor carrier is connected to a non-sterile part of the instrument, and the sensor carrier itself need not be sterile either. Upon attaching the sensor carrier to the non-sterile proximal portion of the instrument, the removable protection device still encapsulates the sterile distal portion of the needle-like instrument, such that this sterile distal portion is not inadvertently contaminated by the non-sterile sensor carrier. Only after attaching the sensor carrier to the non-sterile part of the instrument, the protection device is removed.

As described above, when the sensor carrier is connected with said instrument via said connection means, the elongate carrier body extends from the connection point in distal direction. Accordingly, since the sensor is attached to or enclosed by said carrier body close to the distal end thereof, the sensor itself will likewise be located closer to the distal end of the needle-like instrument, or simply put, close to the tip of the needle. This way, it can be ensured that upon operation, i.e. tracking the tip of the needle-like instrument, the sensor will always be located within the navigation field. Moreover, since the sensor is comparatively close to the needle tip, the position of the needle tip can be estimated from the position of the sensor with a comparatively high precision, and in particular, a precision that is higher than in cases where the sensor would e.g. be attached to the proximal handle of the instrument.

In order to derive the position of the needle tip from the position of the sensor, their relative positions need to be known. The usual way to obtain this information would be to carry out calibration measurements. However, according to the invention, the system employs a connection mechanism which allows for connecting or mounting the sensor carrier at a predetermined connection position and with a predetermined orientation of said sensor carrier body with respect to said needle-like instrument, such that when said sensor carrier is connected with said instrument via said connection mechanism, said sensor is automatically located at a predetermined and known position relative to the distal end of said sterile distal portion. This way, no further calibration is needed.

After use, the needle-like instrument can be disposed, while the sensor carrier can be reused with a new needle-like instrument. It is seen that the additional costs for the needle-like instrument to be trackable within the system is minimal. All the expensive components, such as the sensor itself and typically also the more expensive part of the connection mechanism are provided on the sensor carrier, which need not be sterilized and can reused as often as desired. As far as the needle-like instrument is concerned, the only additional requirement is that it comprises the protection device and that it somehow defines the predetermined connection position, both of which can be provided at very low additional costs.

Preferably, the length of the elongate carrier body is such that it extends from said connection position in distal direction by a length of at least 25%, preferably at least 33% and most preferably at least 40% of the length of the distal sterile portion. The further the elongate carrier body extends from said connection position in distal direction, the closer will the sensor be moved to the distal end of the needle-like instrument. However, the extension of the elongate carrier body in the distal direction is of course limited by the insertion depth of the needle-like instrument into the tissue. In addition or alternatively, the length of the elongate carrier body and the location of the sensor within the or with respect to the elongate carrier body is such that, when said sensor carrier is connected with the non-sterile proximal portion, said sensor is located at a position extending beyond the proximal end of said distal sterile portion in longitudinal direction by a distance of at least 15%, preferably at least 23% and most preferably at least 30% of the length of the distal sterile portion.

In various embodiments, the length of the elongate carrier body is such that it extends from said connection position in distal direction by a length of at least 2.5 cm, preferably at least 3.3 cm and most preferably at least 4.0 cm.

When the sensor carrier is connected with the optionally non-sterile proximal portion via said connection mechanism, said elongate carrier body is preferably arranged in parallel with said sterile distal portion to an extent that a longitudinal axis of said elongate carrier body is inclined with respect to a longitudinal axis of said sterile distal portion by an angle of 30° or less, preferably 15° or less.

In preferred embodiments, the distal sterile portion corresponds to a distal needle portion which is suitable for penetrating tissue. In addition or alternatively, said optionally non-sterile proximal portion corresponds to a proximal handle for holding the instrument.

In preferred embodiments, said removable protection device is formed by a cap.

In a preferred embodiment, the connection mechanism comprises a clip on one of said sensor carrier and said optionally non-sterile proximal portion of said needle-like instrument and a clip rest for receiving the clip on the other of said sensor carrier and said optionally non-sterile proximal portion. Using such a clip, the sensor carrier can be easily mounted to and detached from the needle-like instrument without any tools or the like. Using a combination of a clip and the clip rest allows to connect the sensor carrier with the non-sterile proximal portion at a predetermined connection position and with a predetermined orientation of said sensor carrier body with respect to said needle-like instrument. Since the clip is more expensive to provide than a clip rest, the clip is preferably provided on the sensor carrier which is to be reused, while the clip rest is formed on the needle-like instrument, particularly on its handle, since the needle-like instrument is typically to be disposed after use. In this embodiment, the clip rest defines the aforementioned connection position. Note that in some embodiments, the "clip rest" is specifically provided on the needle-like instrument. In other embodiments, however, structural features on already existing needle-like instruments, such as indentations on the handle or the like, can be used as the "clip rest", and the clip can be designed such as to cooperate with this structural feature. Accordingly, by suitably devising the clip or other type of adapter provided on the sensor carrier, even ordinary commercially available needlelike instruments can be employed in a system according to an embodiment of the invention.

Instead of a clip connection, the connection mechanism may comprise any other suitable type of mechanism that allows for releasably connecting the sensor carrier with the non-sterile proximal portion at a predetermined connection position and with a predetermined orientation of the sensor carrier body with respect to the needle-like instrument. For example, the connection mechanism may be formed by a screw connection, in which the two components are removably fastened to each other using one or more screws. However, other types of latch connections or snap connections are likewise possible.

As indicated above, in preferable embodiments the needle-like instrument is a disposable article, and the sensor carrier is a reusable article.

The invention further provides for a sensor carrier for use in a system according to one of the aforementioned embodiments, wherein:

said sensor carrier comprises an elongate carrier body having proximal and distal ends, a sensor is attached to or enclosed by said carrier body close to its distal end, wherein said sensor is suitable for carrying out measurements allowing for determining the position of the sensor within an electromagnetic navigation field, and said sensor carrier comprises an adapter allowing to releasably connect said sensor carrier with an optionally non-sterile proximal portion of a needle like instrument at a connection position and with a predetermined orientation of said sensor carrier body with respect to said needle-like instrument, such that when said sensor carrier is connected with said instrument via said adapter, said elongate carrier body extends from said connection position in distal direction, and said sensor is automatically located at a predetermined and known position relative to the distal end of said sterile distal portion.

Such a sensor carrier can be commercialized separately from the needle-like elements, and can cooperate with various types of needle-like elements. The sensor carrier comprises an adapter allowing to releasably connect the sensor carrier with the optionally non-sterile proximal portion of such needle-like instruments, which adapter could be any means that allows for this function. For example, the aforementioned clip would be regarded as an "adapter", and the clip rest on the needle-like instrument would be regarded as a further adapter, such that the adapters in combination form said connection mechanism.

The present invention further provides a set comprising a sensor carrier as described above and a needle-like element, wherein said needle-like element has a sterile distal portion and an optionally non-sterile proximal portion, a removable protection device for encapsulating the sterile portion, and an adapter at a predetermined connection position located on said optionally nonsterile portion, wherein the adapters of said needle-like element and said sensor carrier together form a connection mechanism.

Herein the "adapter" of the needle-like instrument can be very simple, as long as it allows for defining the predetermined connection position located on the optionally non-sterile portion. In the simplest case, it could simply be a visually marked portion indicating the predetermined connection position. However, the adapter of the needle-like instrument could be a recess for receiving a portion of the adapter of the sensor carrier, such as the aforementioned clip rest, holes for receiving fastening screws or the like.

SHORT DESCRIPTION OF THE FIGURES

DESCRIPTION OF A PREFERRED EMBODIMENT

Figure 1:
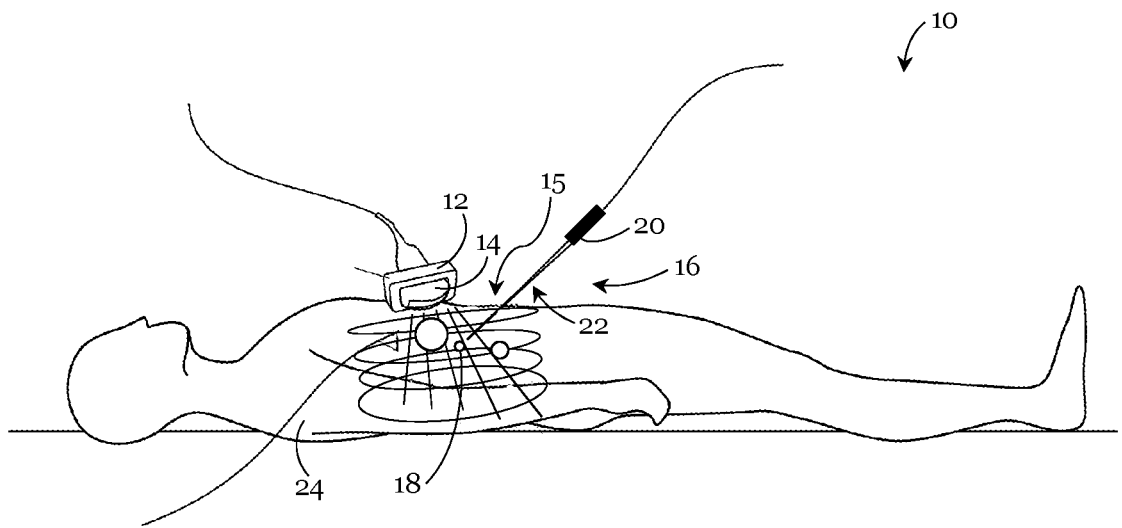
FIG. 1 is a schematic view of a system for navigated punction, biopsy or ablation.

For the purposes of promoting an understanding of the principles of the invention, reference will now be made to a preferred embodiment illustrated in the drawings, and specific language will be used to describe the same. It will nevertheless be understood that no limitation of the scope of the invention is thereby intended, such alterations and further modifications in the illustrated apparatus and such further applications of the principles of the invention as illustrated therein being contemplated as would normally occur now or in the future to one skilled in the art to which the invention relates.

FIG. 1 is a schematic view of a system 10 for navigated punction, biopsy or ablation. The system comprises a mobile electromagnetic field generator 12 which is connected to an ultrasound probe 14. The electromagnetic field generator 12 is configured for generating an electromagnetic field 15 which is referred to as "navigation field" herein.

Also shown in FIG. 1 is a conventional needle 16, which can be used for function or biopsy. While not shown in FIG. 1, the needle 16 could also be provided with a probe for radiofrequency ablation. The needle 16 has a tip 18 at its distal end and a handle 20 at its proximal end. Between the distal end 18 and the handle 20 extends a distal needle portion 22 which is suitable for penetrating the tissue of a patient 24.

The navigated system 10 allows for localizing the position and orientation of a sensor (not shown in FIG. 1) within the navigation field 15. Accordingly, if a sensor is integrated with or attached to the needle 16, and if the position of the sensor with respect to the needle 16 is known, then the needle itself can be tracked by means of the navigation field 15.

The most obvious way to provide the sensor would be to integrate it into the tip 18 of the needle 16 because it is mainly the tip of the needle 16 that needs to be tracked. However, this calls for specially designed needles, which would typically be quite costly, and this would in particular make the use of disposable needles 16 unattractive.

It would also be conceivable to removably attach the sensor to the distal needle portion 22, such that after use and disposal of the needle 16, at least the sensor could be reused. However, if the sensor was attached to the distal needle portion which is sterile under use, the sensor must likewise be sterile, making the reuse of the sensor difficult.

Further, it would be possible to removably attach the sensor to the handle 20. This would at first sight be attractive, because the handle 20 need not necessarily be sterile, and the sensor would hence not have to be sterile either when attached to the handle. However, the inventors have found that when the sensor was attached to the handle, the precision of the tracking of the tip 18 of the needle 16, based on the tracking of the sensor, tends to become insufficient. Namely, due to the large distance between the sensor and the tip 18 of the needle 16, a moderate error in the determination of the position of the sensor will translate to a considerable error in the estimated position of the tip 18 of the needle 16, due to the leverage. Moreover, as is also indicated in FIG. 1, the navigation field 15 provided by the mobile field generator 12 has a limited reach, such that a sensor located on the handle 20 of the needle 16 may be outside the operable range of the navigation field 15. Note that this is different from ordinary tracking mechanisms with what is referred to as "external field generators", i.e. field generators that are provided somewhere in the operation theater rather than on the ultrasound probe 12, wherein the reach of the navigation fields would not be a problem.

Figure 2:
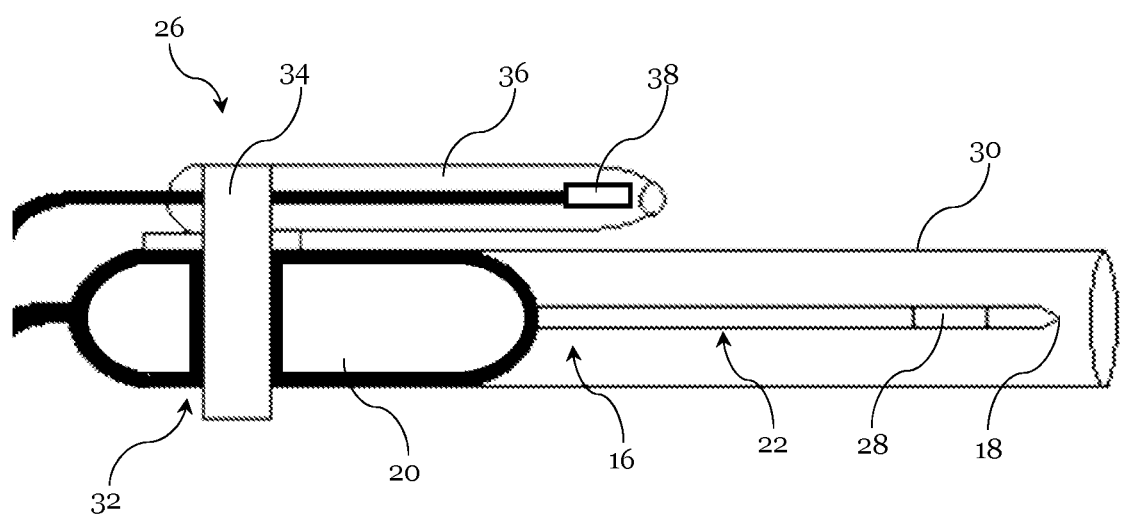
FIG. 2 is a schematic view of a set comprised of a sensor carrier according to one embodiment of the present invention and a needle like element.

FIG. 2 shows an embodiment of a needle 16 and a sensor carrier 26 according to an embodiment of the invention. As is seen in FIG. 2, the needle 16 comprises a distal needle portion 22, which is suitable for penetrating the tissue of the patient 24, and which hence needs to be sterile. The distal needle portion 22 hence is an example of the aforementioned "sterile distal portion". At the distal end of the distal needle portion 22, a sharp needle tip 18 is provided. Further shown in FIG. 2, close to the tip 18, is a radiofrequency ablation probe 28 which allows for radiofrequency ablation in a manner per se known from prior art.

With further reference to FIG. 2, the needle 16 comprises a handle 20, which in use does not need to be sterile. The handle 20 is an example of the aforementioned "optionally non-sterile proximal portion". It is referred to as "optionally" non-sterile, since it need not be sterile, although it is of course not excluded that it is made sterile if desired. The term "optionally non-sterile distal portion" hence is only meant to designate a portion of the needle 16 which does not necessarily have to be sterile under use, as is e.g. the case for the sterile distal needle portion 22.

Further shown in FIG. 2 is a cap 30 which encloses the sterile distal needle portion 22. The cap 30 ensures that when mounting the removable sensor carrier 26 to the handle 20 of the needle 16, the sterile distal needle portion 22 will not be contaminated by accident. Once the sensor carrier 26 is mounted in place, the cap 30 can be removed.

The sensor carrier 26 is releasably connected with the handle 20 of the needle 16 by means of a connection mechanism 32, which in the embodiment shown in FIG. 2 comprises a clip 34 provided on the sensor carrier 26 and a clip rest (not shown in FIG. 2) on the handle 20 to which the clip 34 engages. The clip rest is formed by an angular recess for receiving the clip 34, and which defines a predetermined connection position and also a predetermined orientation of an elongate sensor carrier body 36 with respect to the needle 16.

As is seen in FIG. 2, when the sensor carrier 26 is connected with the needle 16 via said connection mechanism 32, the elongate carrier body 36 extends from the connection position in distal direction. Enclosed in said sensor body 36, close to a distal and thereof, is an electromagnetic sensor 38 which allows for carrying out a measurement of the navigation field 15 allowing for determining the position of the sensor 38 within said navigation field 15. Since the elongate extends to the distal direction, the sensor 38 is located closer to the tip 18 at the distal end of the needle 16 as would e.g. be the case for a sensor that was integrated with a directly attached to the handle 20. In fact, with respect to the longitudinal direction of the needle 16, the position of the sensor 38 overlaps with the sterile distal portion 22, without itself having to be sterile. Accordingly, with the sensor 38 provided in the sensor carrier 32, a high tracking precision can be obtained even in view of a locally restricted navigation field 15.

Moreover, the connection mechanism 32 is devised such that upon connecting the sensor carrier 26 with the needle 16, the sensor is automatically located at a predetermined and known position relative to the distal end 18 of the needle. This is because the clip rest (not shown in FIG. 2) and the clip 34 are devised for cooperating in a way that allow only a single unique way of attachment, which both defines the connection position as well as the orientation of the elongate carrier body with respect to the needle 16. In particular, as indicated in FIG. 2, the clip 34 has a considerable width which avoids a pivoting motion of the elongate body 36 of the sensor carrier 26 and hence ensures that the elongate body 36 will be arranged in parallel to the longitudinal axis of the needle 16 when attached via the clip 34 and the clip rest. Note that the clip rest and the clip 34 resemble examples of the "adapters" referred to in the introductory portion of the description. Moreover, both the needle 16 and the sensor carrier 26 are manufactured to precision, so that the relative position of the sensor 38 and the tip 18 of the needle 16 are predetermined by the structure of the components, such that no additional calibration by the user is necessary. This facilitates the use of the system, and also avoids errors by the user.

Note that, as mentioned before, in some embodiments certain features of already existing needles can be employed as a "clip rest", for example and indentation in a needle handle or the like, to which then the clip, or more generally any type of adapter provided on the sensor carrier would be adapted.

The skilled person will appreciate that many other connection mechanisms than the connection mechanism 32 shown in FIG. 2 are possible, which will likewise lead to a predetermined and reproducible position of the sensor 38 with respect to the tip 18 of the needle 16. In particular, the connection mechanism could employ screws for attaching the sensor carrier 26 to the handle 20, where holes for receiving the screws could be provided in the handle 20 and in a portion of the sensor carrier 26. Note that such holes for receiving corresponding screws would be a further example of an "adapter" as referred to in the introductory portion of the specification. Moreover, other types of adapters for providing any suitable type of latch connection or snap connection may be employed.

Although a preferred exemplary embodiment is shown and specified in detail in the drawings and the preceding specification, these should be viewed as purely exemplary and not as limiting the invention. It is noted in this regard that only the preferred exemplary embodiment is shown and specified, and all variations and modifications should be protected that presently or in the future lie within the scope of protection of the invention as defined in the claims.

REFERENCE LIST 10 system for navigated punction, biopsy or ablation
12 mobile electromagnetic field generator
14 ultrasound probe
15 navigation field
16 needle
18 tip of the needle 16
20 handle of needle 16
22 sterile distal portion of needle 16
24 patient
26 sensor carrier
28 radiofrequency ablation probe
30 protection cap
32 connection mechanism
34 clip
36 elongate sensor carrier body
38 sensor

The invention claimed is:

1. A system for navigated punction, biopsy or ablation comprising:
   a mobile electromagnetic field generator for generating an electromagnetic navigation field, wherein the electromagnetic field generator is physically connected to an ultrasound probe for medical imaging,
   a needle-like instrument, comprising a sterile distal portion and an optionally non-sterile proximal portion, wherein said sterile distal portion comprises a portion of the needle-like instrument that comes into contact with a patient's tissue upon use of said system and therefore must be sterile prior to use of said system, wherein said needle-like instrument comprises an adapter at a predetermined connection position located on said optionally non-sterile portion,
   a removable protection device for encapsulating the sterile distal portion,
   a sensor suitable for carrying out measurements allowing for determining the position of the sensor within said navigation field, and
   a sensor carrier, in addition to said needle-like instrument, wherein:
      said sensor carrier comprises an elongate carrier body having proximal and distal ends,
      said sensor is attached to or enclosed by said carrier body close to its distal end, and
      a further adapter allowing to releasably connect said sensor carrier, together with said sensor attached to or enclosed by said sensor carrier body, with said optionally non-sterile proximal portion of said needle-like instrument, wherein the adapters of said needle-like instrument and said sensor carrier together form a connection mechanism allowing to releasably connect said sensor carrier, together with said sensor attached to or enclosed by said sensor carrier body, with said optionally non-sterile proximal portion of said needle-like instrument at said predetermined, reproducible connection position defined by said adapter of said needle-like instrument and with a predetermined, reproducible orientation of said sensor carrier body with respect to said needle-like instrument, wherein said adapters are devised for cooperating in a way that allow only a unique way of attachment, which both defines the connection position as well as the orientation of the elongate carrier body with respect to the needle such that when said sensor carrier is connected with said needle-like instrument via said connection mechanism,
      said elongate carrier body extends from said connection position in distal direction, and
      said sensor is automatically located at a predetermined, known and reproducible position relative to the distal end of said sterile distal portion, wherein when said sensor carrier is connected with the optionally non-sterile proximal portion via said connection mechanism, said elongate sensor carrier body is arranged beside said needle-like instrument,
   said system configured for tracking the distal end of said sterile portion based on said sensor carrying out measurements for determining the position of said sensor within said electromagnetic navigation field generated by said mobile electromagnetic field generator physically connected to said ultrasound probe, and
   said known and reproducible position of said sensor relative to the distal end of said sterile distal portion.

2. The system of claim 1, wherein the length of the elongate carrier body is such that it extends from said connection position in distal direction by a length of at least 25% of the length of the distal sterile portion, and/or such that, when said sensor carrier is connected with the non-sterile proximal portion, said sensor is located at a position extending beyond the proximal end of said distal sterile portion in longitudinal direction by a distance of at least 15% of the length of the distal sterile portion.

3. The system of claim 1, wherein the length of the elongate carrier body is such that it extends from said connection position in distal direction by a length of at least 2.5 cm.

4. The system of claim 1, wherein when said sensor carrier is connected with the optionally non-sterile proximal portion via said connection mechanism, said elongate carrier body is arranged in parallel with said sterile distal portion to an extent that a longitudinal axis of said elongate carrier body is inclined with respect to a longitudinal axis of said sterile distal portion by an angle of 30° or less.

5. The system of claim 1, wherein said distal sterile portion corresponds to a distal needle portion which is suitable for penetrating tissue.

6. The system of claim 1, wherein said optionally non-sterile proximal portion corresponds to a proximal handle for holding the instrument.

7. The system of claim 1, wherein said removable protection device is formed by a cap.

8. The system of claim 1, wherein one of said adapters of said needle-like instrument and said sensor carrier is formed by a clip and the other of said adapters is formed by a clip rest for receiving said clip.

9. The system according to claim 8, wherein said clip is provided on said sensor carrier and said clip rest is formed on said handle, said clip rest defining said connection position.

10. The system of claim 1, wherein said connection mechanism comprises a screw connection, wherein one of said adapters comprises one or more screws and the other of said adapters comprises one or more holes for receiving said one or more screws, or wherein said connection mechanism comprises a latch connection or a snap connection.

11. The system of claim 1, wherein said needle-like instrument is a disposable article, and said sensor carrier is a reusable article.

\* \* \* \* \*